United States Patent
Sugiyama et al.

(10) Patent No.: US 6,605,704 B1
(45) Date of Patent: Aug. 12, 2003

(54) PLANT-ORIGIN REGULATOR PROTEIN AND NUCLEIC ACID ENCODING THE SAME

(75) Inventors: Tatsuo Sugiyama, Nisshin (JP); Hitoshi Sakakibara, Mukou (JP); Chika Ito, Toyota (JP); Megumi Suzuki, Okazaki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/308,386

(22) PCT Filed: Sep. 18, 1997

(86) PCT No.: PCT/JP97/03290

§ 371 (c)(1),
(2), (4) Date: Jul. 21, 1999

(87) PCT Pub. No.: WO99/14332

PCT Pub. Date: Mar. 25, 1999

(51) Int. Cl.$^7$ .................. A61K 35/78; C07K 14/00; C07H 21/02; C07H 21/04
(52) U.S. Cl. .................. 530/370; 530/350; 530/324; 536/23.1; 536/23.6
(58) Field of Search ............... 530/350, 324, 530/370; 536/23.1, 23.6

(56) References Cited

PUBLICATIONS

Kakimoto, Tatsuo, "Arabidopsis thaliana mRNA for histidine kinase homolog, complete cds", Database: IntelliGenetics, Accession NO: D87545, Feb. 7, 1999.*
The Japanese Society of Plant Physiologist, Plant & Cell Physiology, vol. 38 Supplement, 1997, p. Nos. s64 and s65, Abstract Nos. 210 (2aD08) and 211 (2aD09).
Ursula Kües et al., Microbiological Reviews, vol. 53, No. 4, p. 491–516, Dec. 1989.
Peng Liang et al., Science, vol. 257, p. 967–971, Aug. 14, 1992.
Bambang Sugiharto et al., Plant Physiol., vol. 92, p. 963–969, 1990.
Mark J. Zoller et al., Nucleic Acids Research, vol. 10, No. 20, p. 6487 and 6500, 1982.
Iwane Suzuki et al., Plant Physiol. vol. 105, p. 1223–1229, 1994.
Lisa A. Alex et al., TIG, vol. 10, No. 4, p. 133–138, Apr. 1994.
Caren Chang et al., Science, vol. 262, pp. 539–544, Oct. 22, 1993.
Jian Hua et al., Science, vol. 269, p. 1712–1714, Sep. 22, 1995.
Jack Q. Wilkinson et al., Science, vol. 270, p. 1807–1809, Dec. 15, 1995.
Tatsuo Kakimoto et al., Science, vol. 274, p. 982–985, Nov. 8, 1996.
H. Sakakibara, *Plant Physiology*, vol. 114, No. 3 Suppl., p. 117, Abstract No. 523 (1997).
Plant Physiology, Vol. 114, No. 3, SUPPLY. (Jul. 1, 1997), Sakakibara H. et al, p. 117 Abstract No. 523.
Sakakibara et al., The Plant Journal (1998) 14(3), 337–344.

* cited by examiner

*Primary Examiner*—Christopher S. F. Low
*Assistant Examiner*—Rita Mitra
(74) *Attorney, Agent, or Firm*—Birch, Stewart, Kolasch & Birch, LLP

(57) ABSTRACT

A regulator protein of a two-component signal transduction system in plants and a nucleic acid coding therefor are disclosed. The present invention provided an isolated protein having the amino acid sequence shown in SEQ ID NO:1 in the Sequence Listing or an amino acid sequence having a homology of not less than 30% to the amino acid sequence shown in SEQ ID NO:1, which functions as a regulator protein in a plant, and a nucleic acid coding therefor.

9 Claims, 1 Drawing Sheet

```
maize CIP1   1: MAAAAPAPAPASVAPSSAPKATGDSRKTVVSVDASELEKHVLAVDDSSVDRAVIARITRGSR
ECOcheY      1:                                MADKELKFLVVDDFSTMRR-IVRNLKEL
STYNTRrr     1:                                MQRGIVWVDDSS-IRWVLERALACAG
                                                                    * maize CIP1  61: YRVTAVESATRAIELIALGLLPDVSMIITDYWMPGMTGYELLKCVKESAALRGIPVVIMS
ECOcheY     29: GFNN-VEEAEDGVDAINKLQAGGYGFVISDWNMPNMDGLELLKTIRADGAMSALP-VLMV
STYNTRrr    28: LTCTTFENGNEVLAALA-SKTPDV-L-LSDIRMPGMDGLALLKQIKQRHPM---LPVIIM-
                           ⊛                                     * maize CIP1 121: SENV-PTRITRCLEEGAECFLKPVRPADVSRLCSRIR*
ECOcheY     87: TAEAKKENIIAAAQAGASGYVVKPFTPATLEEKLNKIFEKLGM*
STYNTRrr    82: TAHSDLDAAVSAYQQGAFDYLPKPFDIDEAVALVERAISHYQE----DNA binding region ECOcheY: E.coli CheY [Microbiol. Rev.(1989) 53, 450-490]
STYNTRrr: S.typhimurium NtrC receiver region [Biochemistry (1993) 32, 11741-11753]
```

Fig. 1

PLANT-ORIGIN REGULATOR PROTEIN AND NUCLEIC ACID ENCODING THE SAME

This application is the national phase under 35 U.S.C. §371 of PCT International Application No. PCT/JP97/03290, which has an International filing date of Sep. 18, 1997, which designated the United States of America.

TECHNICAL FIELD

The present invention relates to a regulator protein involved in a plant two-component signal transduction system and to a nucleic acid coding for the same.

BACKGROUND ART

Cytokinins are a group of plant hormones, and have important roles in controlling growth, morphogenesis and flow of nutrients in plants. However, the mechanism by which a cytokinin is recognized by plant cells and causes various actions was not known. As a cytokinin, zeatin is well-known.

Inorganic nutrients including nitrogen largely influence on the growth and morphogenesis of plants. For example, in photosynthetic tissues of maize, enzymes related to C4 photosynthesis such as phosphoenolpyruvate carboxylase (PEPC) are synthesized and accumulated depending on the amount of inorganic nitrogen absorbed from the roots (B. Sugiharto, K. Miyata, H. Nakamoto, H. Sasakawa, T. Sugiyam, Plant Physiol. 92:963, 1990). Sugiharto et al. (B. Sugiharto, J. N. Burnell, T. Sugiyama, Plant Physiol. 100:153, 1992) and Suzuki et al. (I. Suzuki, C. Cretin, T. Omata, T. Sugiyama, Plant Physiol. 105:1223, 1994) discovered that this synthesis and accumulation are caused by the promotion of expression of C4Ppc1, a gene encoding phosphoenolpyruvate carboxylase (PEPC), by a cytokinin. Cytokinins are plant hormones synthesized in roots (L. J. Feldmn, in The Development and Function of Roots, J. G. Torrey and D. T. Clarkson Eds., Academic Press, London, 1975, pp.55–72), and thus it was found that they are important signal substances which transmit the information about the amount of the inorganic nitrogen, that was sensed by the roots.

When bacteria respond to various stimulations from outside, signal transduction mechanism called two-component signal transduction system plays an important role. It has become clear that the two-component signal transduction system is an important signal transduction system also in protozoa, fungi and plants (L. A. Alex and M. I. Simon, Trends Genet. 10:133, 1992). The two-component signal transduction system is composed of a sensor protein which senses stimulations in the outside, and a regulator protein which mediates the signal and causes various reactions. The signal transduction from the sensor protein to the regulator protein is mediated by phosphorylation reaction. The sensor protein serves as a kinase specific to the regulator protein, and the regulator protein is modified by the phosphorylation. The regulator protein is activated by phosphorylation and causes specific gene expression or the like. The sensor protein has a region in the N-terminal region, which senses the stimulation and a transmitter region in the C-terminal region, that phosphorylates the regulator protein. The regulator protein has a receiver region in the N-terminal region, which is phosphorylated, and a region in the C-terminal region, that has an enzyme activity, DNA-binding activity or the like for causing various reactions.

Known plant proteins related to the two-component signal transduction system include the following:

ETR1: This protein is a kind of receptor proteins of ethylene in Arabidopsis. This protein is a kind of sensor proteins and has a region homologous to receiver regions of regulator proteins (C. Chang, S. K. Kwok, A. B. Bleecker, E. M. Meyerowits, Science 262:539–544, 1993).

ERS: This protein is a kind of ethylene receptor proteins of Arabidopsis and a kind of sensor proteins. Its ethylene-receiving region and the transmitter region have high homologies to those of ETR 1. It does not contain a region homologous to the receiver region (J. Hua, C. Chang, Q. Sun, E. M. Meyerowitz, Science 269:1712–1714, 1995).

NR: This protein is an ethylene receptor protein of tomato. This protein has a high homology to ETRI but does not have a region homologous to the receiver region, like ERS (J. Wilkinson, M. B. Lanahan, H.-C. Yen, J. J. Giovannoni, H. J. Klee, Science 270:1807–1809, 1995).

CKI1: This protein is thought to be a cytokinin receptor protein of Arabidopsis and is a kind of sensor proteins. This protein has a region homologous to the receiver region like ETRI, in addition to the cytokinin receptor region and a transmitter region (T. Kakimoto, Science 274:982–985, 1996).

Thus, those hitherto known in plants are sensor proteins similar to the sensor proteins of microorganisms or sensor proteins which have regions homologous to the receiver region of a regulator protein. Thus, no plant regulator proteins are known.

Thus, it has been suggested that the signal transduction system in plants are composed of proteins and mechanisms having considerably different properties from those involved in the signal transduction system of microoganisms.

On the other hand, if a protein or a DNA encoding a protein in a plant is known, a protein resulting from modification of the protein may be expressed in plants, expression of the protein in the plant may be inhibited, the protein may be expressed in excess, or expression control of the protein may be modified by using recombinant DNA technology and the technology to construct transgenic plants.

Therefore, if a protein in a signal transduction system is known, manipulation of the signal tansduction system may be possible, and in turn, various life phenomena downstream thereof may be manipulated.

DISCLOSURE OF THE INVENTION

An object of the present invention is to provide a regulator protein in a two-component signal trnasduction system of a plant and a nucleic acid coding therefor.

The present inventors isolated a cDNA of a gene specifically induced by a cytokinin, from green leaves of maize in nitrogen-deficient state by using differential display method; sequenced the cDNA and determined the amino acid sequence of the protein encoded by the cDNA; discovered that the amino acid sequence has a homology to regulator proteins of microorganisms and that the amino acid sequence has characteristic amino acids common to regulator proteins of microorganisms; and confirmed that the gene is induced by nitrogen or a cytokinin; thereby confirming that the protein is a regulator protein, to complete the present invention.

That is, the present invention provides an isolated protein having the amino acid sequence shown in SEQ ID NO:1 in the Sequence Listing or an amino acid sequence having a homology of not less than 30% to the amino acid sequence shown in SEQ ID NO:1, which functions as a regulator protein in a plant. The present invention also provides an isolated nucleic acid encoding the protein of the present invention.

Only sensor proteins are known as proteins involved in two-component signal transduction systems of plant cells. In monocotyledons, even a protein involved in a two-component signal transduction system is not known. Thus, by the present invention, a regulator protein of a two-component signal transduction system of plant cells and a nucleic acid coding therefor were first provided. Especially, a protein in a two-component signal transduction system in monocotyledon was first provided by the present invention. Thus, by the present invention, the signal transduction system of a cytokinin may be effectively modified by manipulation of the two-component signal transduction system so as to effectively control the various physiological mechanisms.

BRIEF DESCRIPTION OF THE DRAWINGS

FIG. 1 shows the amino acid sequence of CIP 1 (SEQ ID NO:1) which is an example of the regulator protein according to the present invention in comparison with the amino acid sequence of CheY (SEQ ID NO:3) which is a regulator protein originated from *E. coli* and that of STYNTRrr (SEQ ID NO:4) which is a regulator protein originated from *Salmonella typhimurium*.

BEST MODE FOR CARRYING OUT THE INVENTION

The nucleic acid according to the present invention, which codes for a regulator protein of a plant was obtained by the method detailed in the Examples below. Briefly, cDNA libraries were prepared from maize green leaves treated with zeatin which is a kind of cytokinins and maize green leaves not treated with zeatin, respectively. Using these cDNA libraries as templates, DNAs were amplified by PCR using random primers (radiolabelled dCTP was used so that amplification products are radiolabelled), and the amplification products were fractionated by electrophoresis, followed by isolation of the cDNA from the gel, which is expressed in the green leaves treated with zeatin but not expressed in the green leaves not treated with zeatin. Using this partial length cDNA as a probe, the cDNA library originated from the maize green leaves treated with zeatin was screened to obtain a full length cDNA clone ZmCip1.

The nucleotide sequence of ZmCip1 cDNA is shown in SEQ ID NO: 2 in the Sequence Listing. It was proved that the nucleotide sequence of ZmCip1 cDNA contains an open reading frame encoding a protein with a size of 16.7 kDa having 157 amino acids, as shown in SEQ ID NO: 2. The amino acid sequence alone shown in SEQ ID NO: 2 is shown in SEQ ID NO: 1. This protein was named CIP1 (abbreviation of cytokinin-induced protein).

The amino acid sequence of CIP1 has a high homology to the receiver region of CheY (U.Kues, U. Stahl, Microbiol. Rev. 53:491, 1989) (FIG. 1) which is a kind of regulator proteins of microoganisms. CIP1 has the amino acid residues corresponding to Asp90 residue presumed as the phosphate binding site, and corresponding to Asp44 residue and Lys142 residue in the active site, which amino acid residues are located in the regions in CheY, that have high homologies to other regulator proteins. CheY is the most analyzed regulator protein. The amino acid sequence of CIP1 has a homology of 47% to that of CheY, and has a 42% homology to the receiver region of CKI1 which is a cytokinin receptor protein of Arabidopsis. The N-terminal region of CIP 1 is unique to CIP1 and is considerably longer than that of CheY. The amino acid sequence of CIP1 is shown in FIG. 1 in comparison with that of CheY from *E. coli* and that of STYNTRrr from *Salmonella typhimurium*, which are regulator proteins of microorganims.

As concretely described in the Examples below, it was experimentally confirmed that expression of CIP1 gene in plant leaves is induced by a cytokinin and an inorganic nitrogen such as nitrate ion or ammonium ion, and is not induced in roots. From these data and the above-described homologies of the sequences, it was clarified that CIP1 encoded by ZmCip1 cDNA is a regulator protein originated from a plant.

It is well-known in the art that there are cases wherein the physiological activity of a physiologically active protein is retained even if one or more amino acids in the amino acid sequence are substituted or deleted, or even if one or more amino acids are added to or inserted into the amino acid sequence. Therefore, proteins having the same amino acid sequence as shown in SEQ ID NO: 1 except that one or more amino acid residues are substituted or deleted, or one or more amino acid residues are added to or inserted in the amino acid sequence, which amino acid sequence has a homology of not less than 50% to that shown in SEQ ID NO: 1, which proteins function as regulator proteins in a plant, as well as the nucleic acids coding for these proteins, are within the scope of the present invention. The above-mentioned homology is preferably not less than 70%, more preferably not less than 80%, more preferably not less than 90% and more preferably not less than 95%. It is preferred that the aspartic acid residue which is the 44th amino acid residue, the aspartic acid which is the 90th amino acid residue, and the lysine residue which is the 142nd amino acid residue in the sequence shown in SEQ ID NO: 1 be conserved. Introduction of the above-mentioned substitution, deletion, insertion and addition of amino acid residues to an amino acid sequence of a protein may be attained by the well-known site-specific mutagenesis (Nucleic Acid Research, Vol. 10, No. 20, p6487–6500, 1982). By repeating the site-specific mutagenesis, it is possible to construct a nucleic acid and protein having a relatively low homology.

The regulator protein according to the present invention is a regulator protein of a two-component signal transduction system involved in signal transduction by a cytokinin in plant cells. Therefore, by expressing the gene of the regulator protein according to the present invention under an appropriate promoter as a sense or antisense gene by using the recombinant DNA technology, the technology to construct transgenic plants or the like, the signal transduction by a cytokinin may be turned-on and turned-off in a particular tissue at a particular time. As a result, germination, growth, morphogenesis, photosynthesis, stress-resistance, flowering/fructification, dormancy, senescence or the like may be controlled, so that novel varieties having high productivity, high quality, stress-resistance and/or pest-resistance may be developed. For example, since cytokinins have senescence-inhibition activities in plants, by expressing the gene of the regulator protein according to the present invention under control of a promoter such as the 35S promoter of cauliflower mosaic virus or the like, which systemically expresses genes in plants or a promoter which expresses genes in senescence, the signal by a cytokinin may be transmitted in plant tissues even in senescence period, so that expression of the genes encoding proteins related to photosynthesis may be promoted or retained, whose expression is otherwise reduced in aging. Thus, by this method, novel varieties which attain increased biomass or yields may be developed. Further, since cytokinins have an activity to initiate the growth of dormant buds of potato tubers, by expressing the gene of the regulator protein according to the present invention as an antisense gene under control of a promoter that expresses genes in stored tubers after harvest so as to stop the transduction of the cytokinin signals, a novel potato variety in which germination of tubers is inhibited and dry weight loss is decreased, which may be stored for a long time, may be created.

The invention will now be described more concretely by way of examples.

It should be noted that the present invention is not limited to the examples below.

EXAMPLES (1) Isolation of Partial Length cDNA Clone of Cytokinin-induced Gene by Differential Display Method Maize (Zea mays L.cv. Golden Cross Bantam T51) was cultivated in a growth chamber under nitrogen condition (0.8 mM $NaNO_3$) for 18 days as reported (B. Sugiharto, K. Miyata, H. Nakamoto, H. Sasakawa, T. Sugiyama, Plant Physiol. 92:963, 1990). The youngest expanded leaves were cut at the distal end of the leaf blade in water by using razorblade. Thereafter, the leaves were placed in a beaker containing water with and without 5 μM t-zeatin, respectively, such that the distal ends of the leaves were downside. These leaves were placed in the above-mentioned growth chamber for 40 minutes or 90 minutes. Thereafter, lower half of each leaf was collected and frozen with liquid nitrogen. From about 15 leaves, total RNAs were prepared by the guanidine thiocyanate/cesium chloride method.

Using a commercially available kit (RNAamp (trademark), Genhunter), differential display experiment (P. Liang, A. B. Pardee, Science 257:967, 1992) was carried out for the obtained RNAs in accordance with the instructions attached to the kit. Firstly, from the RNAs, single-stranded cDNA were synthesized by reverse transcription reaction using oligo(dT) primer. The cDNAs were amplified by PCR using various synthetic primers (random primers). The reaction was carried out in the presence of [$\alpha$-$^{32}$P]dCTP to radiolabel the amplification product. After the reaction, the PCR product was fractionated by 6% polyacrylamide gel electrophoresis and autoradiography was carried out. The cDNA whose expression was observed to be induced by the 5 μM t-zeatin was isolated from the gel and cloned into pT7Blue T-vector (trademark, Novagen). By these experiments, a partial length cDNA clone of a cytokinin-induced gene was obtained.

(2) Isolation of Full Length cDNA Clone of Cytokinin-induced Gene and Determination of DNA Sequence of the Same Poly(A)$^+$RNAs from the maize cut leaves treated with t-zeatin for 90 minutes according to the method described above were prepared by a conventional method and a cDNA library was prepared using IMOSEIox vector (trademark, Amersham).

Using the above-described partial length clone as a probe, the cDNA library was screened to obtain a full length cDNA clone ZmCip1. DNA sequence of the ZmCip1 cDNA was determined by a conventional method using a commercially available DNA sequencer. The determined nucleotide sequence is shown in SEQ ID NO: 2 together with the deduced amino acid sequence encoded thereby.

(3) Assay of Induction of Expression of CIP 1 by Cytokinin Treatment (Run-Off Transcription Assay) Run-off transcription assay for expression of ZmCip1 gene was carried out. Nuclei were isolated from maize mesophyll cells and its RNA synthesis activity was measured according to a reported method (I. Suzuki, C. Cretin, T. Omata, T. Sugiyama, Plant Physiol.105:1223,1994). The RNAs synthesized by the isolated nuclei were fractionated by formaldehyde gel electrophoresis and the fractionated RNAs were transferred to a nylon membrane, followed by hybridization with $^{32}$P-labeled ZmCip 1 cDNA or C4Ppc1 cDNA. The intensity of the detected signal was measured by Bio Imaging Analyzer (BAS2000, Fuji Film).

As a result, the treatment of the cut leaves of the maize cultivated under the low- nitrogen condition with t-zeatin for only 20 minutes causes transcription of ZmCip1 mRNA. This transcription occurred at much earlier stage than the transcription of the mRNA of C4Ppc1 coding phosphoenolpyruvate carboxylase (PEPC) in the same leaves treated with t-zeatin.

(4) Analysis of Induction of Expression of CIP1 by Cytokinin Treatment (Northern Analysis)

The cut leaves of the maize cultivated under the low-nitrogen condition as mentioned above was treated with 5 μM t-zeatin or with water for 0 minute, 30 minutes, 45 minutes, 60 minutes or 90 minutes, and the ⅓ portions from the distal ends of the leaves was collected. After freezing the collected leaves with liquid nitrogen, RNAs were extracted by the guanidine thiocyanate/cesium chloride method. Ten micrograms of the obtained RNAs were fractionated by formaldehyde gel (1%) electrophoresis and the resultant was transferred to a nylon membrane. Hybridization was performed using ZmCip1 cDNA or maize ubiquitin gene as a probe.

As a result, accumulation of the mRNA of ZmCip1 was confirmed 30 minutes after the cytokinin treatment in the nitrogen-deficient maize green leaves and it was proved that the gene was strongly expressed 45–90 minutes after the cytokinin treatment. In case where the cytokinin treatment was not performed, the expression was not detected.

(5) Analysis of Induction of Expression of CIP1 by Nitrate Ion (Northern Analysis)

The cut leaves of the maize cultivated under the low-nitrogen condition as mentioned above were treated with 16 mM $NaNO_3$ solution or with 0.08 mM $NaNO_3$ solution for 0 hour, 2 hours, 5 hours, 60 hours or 24 hours and Northern analysis was carried out in the same manner as in (4) except that the weight of the RNAs applied to each gel was 20 μg, respectively, and that a non-coding region of ZmCip1 was used as a probe.

As a result, accumulation of mRNA of ZmCip1 in the nitrogen-deficient green leaves was confirmed 5–6 hours after the nitrate ion treatment, and expression of the gene was scarcely observed 24 hours after the treatment. In case where the nitrate ion treatment was not performed, the expression was not detected.

(6) Analysis of Induction of Expression of CIP1 by Nitrate Ion in Leaves and Roots (Northern Analysis)

The maize cultivated under the low-nitrogen condition as mentioned above was treated with 16 mM $NaNO_3$ solution or with 0.08 mM $NaNO_3$ solution for 5 hours, and its leaf blades, leaf sheaths and roots were separately collected, followed by Northern analysis in the same manner as in (5) except that the amount of the RNAs from leaf sheaths or roots applied to each gel was 30 μg.

As a result, accumulation of mRNA of ZmCip1 was confirmed 5 hours after the nitrate ion treatment in the nitrogen-deficient maize green leaves, while its expression was scarcely observed in roots.

(7) Analysis of Induction of Expression of CIP1 by Ammonium Ion (Northern Analysis)

The cut leaves of the maize cultivated under the low-nitrogen condition as mentioned above were treated with 6 mM $NH_4^+$ solution or with 0.08 mM $NaNO_3$ solution for 0 to 7 hours and Northern analysis was carried out in the same manner as in (5) except that the weight of the RNAs applied to each gel was 15 μg.

As a result, mRNA of ZmCip1 was confirmed 5 hours after the ammonium ion treatment in the nitrogen-deficient maize green leaves and it was proved that the gene was strongly expressed 6 to 7 hours after the treatment. In case where the ammonium ion treatment was not performed, its expression was scarcely detected.

(8) Analysis of Induction of Expression of CIP1 by Cytokinin Treatment and Cycloheximide Treatment (Northern Analysis)

The cut leaves of the maize cultivated under the low-nitrogen condition as mentioned above were treated (i) with water for 60 minutes and then with water for 90 minutes, (ii) with water for 60 minutes and then with 5 μM t-zeatin for 90 minutes, (iii) with 20 μg/ml of cycloheximide for 60 minutes and then with 20 μg/ml cycloheximide and 5 μM t-zeatin for 90 minutes, or (iv) with 20 μg/ml of cycloheximide for 60 minutes and then with 20 μg/ml of cycloheximide for 90 minutes, and Northern analysis was performed in the same manner as in (5) except that the amount of the RNAs applied to each gel was 30 μg.

As a result, mRNA of ZmCip 1 was confirmed 5 hours after the ammonium ion treatment in the nitrogen-deficient maize green leaves and it was proved that the gene was strongly expressed 6 to 7 hours after the treatment. In case where the ammonium ion treatment was not performed, its expression was scarcely detected.

(9) Analysis of Induction of Expression of CIP1 by Treatment with Trace Amount of Cytokinin (Northern Analysis)

The cut leaves of the maize cultivated under the low-nitrogen condition as mentioned above were treated with $10^{-11}$ to $10^{-7}$M t-zeatin solution or water for 100 minutes or 180 minutes and then ⅓ portions from the distal ends of the leaves were collected, followed by the Northern analysis as in (5).

As a result, it was confirmed that expression of mRNA of ZmCip1 was induced by the treatment with a very low level of t-zeatin as low as $10^{-9}$ M.

(10) The cut leaves of the maize cultivated under the low-nitrogen condition as mentioned above were treated with 5 μM t-zeatin, 5 μM benzyladenine, 10 μM±abscisic acid or with water for 100 minutes or 180 minutes, and Northern analysis was performed as in (4).

As a result, it was proved that expression of mRNA of ZmCip1 was induced in the nitrogen-deficient leaves by the benzyladenine treatment as the t-zeatin treatment, and that the expression was slightly induced by the abscisic acid treatment.

(11) Analysis of Induction of Expression of CIP1 by Sugar-bound Cytokinin (Northern Analysis)

The cut leaves of the maize cultivated under the low-nitrogen condition as mentioned above were treated with 5 μM t-zeatin, 5 μM zeatin-O-glucoside or with water for 100 minutes, and Northern analysis was performed in the same manner as in (5), except that the amount of the RNAs applied to each gel was 15 μg.

As a result, it was proved that expression of mRNA of ZmCip1 was induced in the nitrogen-deficient leaves by the zeatin-O-glucoside treatment as the t-zeatin treatment.

Judging collectively from the results of (3) to (11), it is thought that upon sensing nitrogen by the roots, a cytokinin is synthesized in the roots, the cytokinin is flowed to the leaves, expression of the CIP1 protein is induced in the leaves and then expression of the genes related to C4 photosynthesis including C4Ppc1 is caused by the two-component signal transduction system involving the CIP1 protein.

What is claimed is:

1. An isolated protein comprising an amino acid sequence of SEQ ID NO:1 or an amino acid sequence having a sequence identity that is ≧70% to said SEQ ID NO:1, wherein said protein functions as a regulator protein in a plant.

2. The protein of claim 1, wherein the amino acid sequence is SEQ ID NO:1.

3. The protein of claim 1, wherein said protein is from a monocotyledon plant.

4. An isolated nucleic acid coding for the protein of claim 1.

5. The nucleic acid of claim 5, wherein the nucleotide sequence is SEQ ID NO:2.

6. An isolated protein comprising
   a) a first amino acid sequence of SEQ ID NO:1 or
   b) a second amino acid sequence having a sequence identity that is ≧80% to said SEQ ID NO:1,
   wherein the amino acid at position 44 of said second amino acid sequence is aspartic acid, the amino acid at position 90 of said second amino acid sequence is aspartic acid, and the amino acid at position 142 of said second amino acid sequence is lysine, and
   wherein said protein comprising either first amino acid sequence or second amino acid sequence functions as a regulator protein in a plant.

7. The protein of claim 6, wherein said sequence identity is ≧90%.

8. The protein of claim 6, wherein said sequence identity is ≧95%.

9. An isolated protein comprising
   a) a first amino acid sequence of SEQ ID NO:1 or
   b) a second amino acid sequence having 157 amino acid residues with a sequence identity that is ≧70% to said SEQ ID NO:1,
   wherein said protein comprising either first amino acid sequence or second amino acid sequence functions as a regulator protein in a plant and is 16.7 kDa, and
   wherein the amino acid at position 44 of said second amino acid sequence is aspartic acid, the amino acid at position 90 of said second amino acid sequence is aspartic acid, and the amino acid at position 142 of said second amino acid sequence is lysine.

* * * * *

SEQUENCE LISTING

```
<160> NUMBER OF SEQ ID NOS: 4

<210> SEQ ID NO 1
<211> LENGTH: 157
<212> TYPE: PRT
<213> ORGANISM: Maize

<400> SEQUENCE: 1

Met Ala Ala Ala Ala Pro Ala Pro Ala Ser Val Ala Pro Ser Ser Ala
1               5                   10                  15

Pro Lys Ala Thr Gly Asp Ser Arg Lys Thr Val Val Ser Val Asp Ala
            20                  25                  30

Ser Glu Leu Glu Lys His Val Leu Ala Val Asp Asp Ser Ser Val Asp
        35                  40                  45

Arg Ala Val Ile Ala Arg Ile Leu Arg Gly Ser Arg Tyr Arg Val Thr
    50                  55                  60

Ala Val Glu Ser Ala Thr Arg Ala Leu Glu Leu Leu Ala Leu Gly Leu
65                  70                  75                  80

Leu Pro Asp Val Ser Met Ile Ile Thr Asp Tyr Trp Met Pro Gly Met
                85                  90                  95

Thr Gly Tyr Glu Leu Leu Lys Cys Val Lys Glu Ser Ala Ala Leu Arg
            100                 105                 110

Gly Ile Pro Val Val Ile Met Ser Ser Glu Asn Val Pro Thr Arg Ile
```

```
                115                 120                 125
           Thr Arg Cys Leu Glu Glu Gly Ala Glu Gly Phe Leu Leu Lys Pro Val
               130                 135                 140
           Arg Pro Ala Asp Val Ser Arg Leu Cys Ser Arg Ile Arg
           145                 150                 155

<210> SEQ ID NO 2
<211> LENGTH: 813
<212> TYPE: DNA
<213> ORGANISM: Maize
<220> FEATURE:
<221> NAME/KEY: CDS
<222> LOCATION: (76)..(546)

<400> SEQUENCE: 2
ctgtctgttt gcagcacccg caccacctga ctgtctgttt gcagcagccg cacctgtgtc      60
ccgtccgtct ctgca atg gcc gct gcc gca ccg gct cca gca tct gtg gcg     111
               Met Ala Ala Ala Ala Pro Ala Pro Ala Ser Val Ala
                 1               5                  10 ccg tcc tct gcg ccc aag gcc acc ggc gac agc agg aag acg gtg gtg     159
Pro Ser Ser Ala Pro Lys Ala Thr Gly Asp Ser Arg Lys Thr Val Val
        15                  20                  25 tcc gtg gac gcg tca gag ctg gag aag cac gtg ctg gcg gtg gac gac     207
Ser Val Asp Ala Ser Glu Leu Glu Lys His Val Leu Ala Val Asp Asp
 30                  35                  40 agc tcc gtg gac cgt gcc gtg att gct agg atc ctg cgt ggc tcc agg     255
Ser Ser Val Asp Arg Ala Val Ile Ala Arg Ile Leu Arg Gly Ser Arg
 45                  50                  55                  60 tac agg gtg acc gcc gtg gag tcg gcg aca cga gcg ttg gag ctg ctc     303
Tyr Arg Val Thr Ala Val Glu Ser Ala Thr Arg Ala Leu Glu Leu Leu
                 65                  70                  75 gcg ctg ggc ctg ctt ccc gac gtc agt atg atc atc acc gac tac tgg     351
Ala Leu Gly Leu Leu Pro Asp Val Ser Met Ile Ile Thr Asp Tyr Trp
             80                  85                  90 atg ccc ggg atg acc ggg tac gag ctg ctc aag tgc gtc aag gag tcg     399
Met Pro Gly Met Thr Gly Tyr Glu Leu Leu Lys Cys Val Lys Glu Ser
         95                 100                 105 gcg gcg cta agg ggc att ccc gtc gtc atc atg tcg tcg gag aac gtg     447
Ala Ala Leu Arg Gly Ile Pro Val Val Ile Met Ser Ser Glu Asn Val
     110                 115                 120 ccc acc cgt atc acc cgc tgc ctg gag gaa ggc gcc gag ggc ttc ctc     495
Pro Thr Arg Ile Thr Arg Cys Leu Glu Glu Gly Ala Glu Gly Phe Leu
125                 130                 135                 140 ctc aag ccc gtc cgc ccc gcc gac gtc tcc cgc ctc tgc agc cgg atc     543
Leu Lys Pro Val Arg Pro Ala Asp Val Ser Arg Leu Cys Ser Arg Ile
                145                 150                 155 cgg tgactgcgtg tggtgctatg ttaggagcta ggatcctcaa ccaaaaaaaa           596
Arg aagattcctc ttctttcttt ctttctctcc tgcttggaca tagatcttca acaaggagc     656 taacatttgg ggggagactt tttagcttta gggatctcaa caagctgttc ggaacggggg     716
ggatggagca cagcgttggc tgttcttttc tccattcttc ttaataacat caggtgtcaa     776
tgtcatgcac gaaaaaaaaa aaaaaaaaa aaaaaaa                              813

<210> SEQ ID NO 3
<211> LENGTH: 132
<212> TYPE: PRT
<213> ORGANISM: E.coli
<220> FEATURE:
<221> NAME/KEY: UNSURE
```

```
<222> LOCATION: (20)..(20)
<223> OTHER INFORMATION: Xaa = any amino acid, unknown or other
<221> NAME/KEY: UNSURE
<222> LOCATION: (34)..(34)
<223> OTHER INFORMATION: Xaa = any amino acid, unknown or other
<221> NAME/KEY: UNSURE
<222> LOCATION: (85)..(85)
<223> OTHER INFORMATION: Xaa = any amino acid, unknown or other

<400> SEQUENCE: 3

Met Ala Asp Lys Glu Leu Lys Phe Leu Val Val Asp Phe Ser Thr
1               5                   10                  15

Met Arg Arg Xaa Ile Val Arg Asn Leu Leu Lys Glu Leu Gly Phe Asn
            20                  25                  30

Asn Xaa Val Glu Glu Ala Glu Asp Gly Val Asp Ala Leu Asn Lys Leu
        35                  40                  45

Gln Ala Gly Gly Tyr Gly Phe Val Ile Ser Asp Trp Asn Met Pro Asn
    50                  55                  60

Met Asp Gly Leu Glu Leu Leu Lys Thr Ile Arg Ala Asp Gly Ala Met
65                  70                  75                  80

Ser Ala Leu Pro Xaa Val Leu Met Val Thr Ala Glu Ala Lys Lys Glu
                85                  90                  95

Asn Ile Ile Ala Ala Ala Gln Ala Gly Ala Ser Gly Tyr Val Val Lys
            100                 105                 110

Pro Phe Thr Pro Ala Thr Leu Glu Glu Lys Leu Asn Lys Ile Phe Glu
        115                 120                 125

Lys Leu Gly Met
    130

<210> SEQ ID NO 4
<211> LENGTH: 134
<212> TYPE: PRT
<213> ORGANISM: S.typhimurium
<220> FEATURE:
<221> NAME/KEY: UNSURE
<222> LOCATION: (1)..(134)
<223> OTHER INFORMATION: Any Xaa = any amino acid, unknown or other

<400> SEQUENCE: 4

Met Gln Arg Gly Ile Val Trp Val Val Asp Asp Ser Ser Xaa Ile
1               5                   10                  15

Arg Trp Val Leu Glu Arg Ala Leu Ala Gly Ala Gly Leu Thr Cys Thr
            20                  25                  30

Thr Phe Glu Asn Gly Asn Glu Val Leu Ala Ala Leu Ala Xaa Ser Lys
        35                  40                  45

Thr Pro Asp Val Xaa Leu Xaa Leu Ser Asp Ile Arg Met Pro Gly Met
    50                  55                  60

Asp Gly Leu Ala Leu Leu Lys Gln Ile Lys Gln Arg His Pro Met Xaa
65                  70                  75                  80

Xaa Leu Pro Val Ile Ile Met Xaa Thr Ala His Ser Asp Leu Asp Ala
                85                  90                  95

Ala Val Ser Ala Tyr Gln Gln Gly Ala Phe Asp Tyr Leu Pro Lys Pro
            100                 105                 110

Phe Asp Ile Asp Glu Ala Val Ala Leu Val Glu Arg Ala Ile Ser His
        115                 120                 125

Tyr Gln Glu Xaa Xaa Xaa
    130
```